United States Patent [19]

Bernard

[11] Patent Number: 4,618,367
[45] Date of Patent: Oct. 21, 1986

[54] NOVEL HERBICIDAL SALT
[75] Inventor: Milton S. Bernard, Vicksburg, Miss.
[73] Assignee: Vertac Chemical Corporation, Memphis, Tenn.
[21] Appl. No.: 777,368
[22] Filed: Sep. 18, 1985
[51] Int. Cl.$^4$ .................. A01N 31/08; C07C 91/04
[52] U.S. Cl. ...................................... 71/121; 564/280
[58] Field of Search ........................... 564/280; 71/121
[56] References Cited

U.S. PATENT DOCUMENTS 3,493,361  2/1970  Nickell et al. .................... 71/121
4,309,205  1/1982  Kessler ............................. 71/121

FOREIGN PATENT DOCUMENTS 16463    7/1968  Japan ................................ 71/121
25038    7/1971  Japan ............................... 564/280
2091712  8/1982  United Kingdom ............... 71/121

Primary Examiner—J. E. Evans
Attorney, Agent, or Firm—Bierman, Peroff & Muserlian

[57] ABSTRACT

A salt of 6-sec.-butyl-2,4-dinitrophenol and choline of the formula

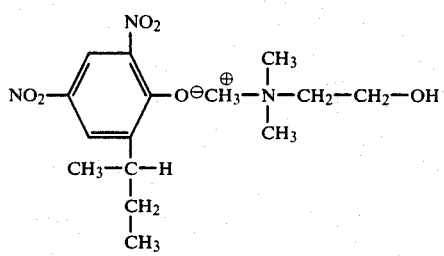

having selective herbicidal activity.

5 Claims, No Drawings

NOVEL HERBICIDAL SALT

STATE OF THE ART

Choline or trimethyl (2-hydroxyethyl)-ammonium hydroxide has not been shown to have any effect on plant cell growth or regulation but certain derivatives have been shown to affect plants. Cycocel or chlorocholine chloride has been shown to increase the sturdiness and compactness of wheat cells. Dinoseb or 2,4-dinitro-6-sec.-butyl-phenol has been used as a herbicide and a corn yield enhancer and has been used in conjunction with the dipropyl-S-ester of carbamothioic acid for weed control. Dinoseb has been used as a herbicide for years, but in making the alkanolamine salt the nitrosamines are formed.

Alkanolamine salts of dinoseb have been used as herbicides but during the salt formation, nitrosodiethanolamine which is a carcinogen is also formed. Currently, there is not a source of alkanolamine available that a dinoseb product could be made from that does not have a secondary amine, such as diethanolamine, present. Choline is a quaternary ammonium compound and does not suffer this defect.

OBJECTS OF THE INVENTION

It is an object of the invention to provide the novel salt of dinoseb and choline and a method of its preparation.

It is another object of the invention to provide novel selective herbicidal compositions and to a novel method of selectively killing weeds in useful crops.

These and other objects and advantages of the invention will become obvious from the following detailed description.

THE INVENTION

The novel salt of the invention is the salt of 6-sec.-butyl-2,4-dinitrophenol and choline of the formula

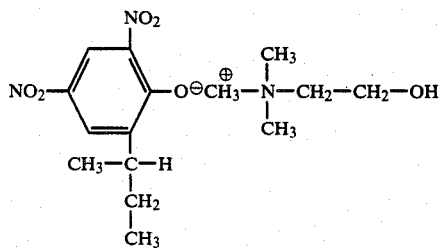

The salt of the invention has the advantage of being an effective selective herbicide comparable to that of alkanolamine salts of dinoseb without the problems thereof.

The novel method of the invention for the preparation of the choline salt of dinoseb comprises admixing approximately stoichiometric amounts of dinoseb and choline, preferably in the presence of a solvent, to form the corresponding salt.

The choline dinoseb salt has shown excellent selectivity and is therefore a useful herbicide with the following useful crops: Cotton, Beans (field, snap, lima), Corn (field, popcorn, sweetcorn), Peanuts, Soybeans, Potatoes, Lentils, Curcurbits, Fruit and nut orchards, Grape vineyards, Peas and Strawberries for control of the following weed species: Cocklebur, Annual Morning glory, Pricky Sida, Sesbania, Threeseed Mercury, Pigweeds, Jimsonweed, Common Ragweed, Annual Smartweed, Velvet Leaf, many other Broadleaf weeds and seedling grasses.

The herbicidal preparations may take the form of dusting preparations or solutions, emulsions or dispersions and may contain the aforesaid salt compounds alone or together with another weed killer, for example, a tri- or tetra-substituted aryl-alkyl-urea, a halogenated phenoxy-alkane-carboxylic acid, a halogenated benzoic acid or phenylacetic acid, a halogenated fatty acid or a salt, ester or amide thereof, or with borax or other inorganic salts, such as abraum salts, or with calcium cyanamide, urea or other fertilizer, or with a pest combatting agent, for example, a chlorinated hydrocarbon or a phosphoric acid ester. Basic active substances, for example, tertiary or quaternary amines having a herbicidal action, may also be added such, for example, as dodecyl-hexamethyleneimine or salts thereof, or 1:1'-ethylene-2:2'-dipyridinium dibromide. There may also be incorporated with the preparation herbicidal carbamates or thiol-carbamates or dithio-carbamic acid esters or derivatives of symmetrical triazines. Herbicidal heterocyclic compounds may also be added, for example, 2-chlorobenzthiazole, 3-amino-1:2:4-triazole, maleic acid hydrazide, 3:5-dimethyl-tetrahydro-1:3:5:2:4-thiadiazine-2-thione, or more simple herbicides, such as pentachlorophenol, dinitrocrescol, dinitro-butyl-phenol, naphthyl-phthalamic acid or methyl isothiocyanate.

In order to prepare a solution suitable for direct spraying there may be used, for example, a mineral oil fraction of high or medium boiling range, such as diesel oil or kerosene, or coal tar oils, or vegetable or animal oils and also hydrocarbons such as alkylated naphthalenes, or tetrahydronaphthalene, if desired, with the use of xylene mixtures, cyclohexanols, ketones, or chlorinated hydrocarbons, such as tetrachlorethane, trichloroethylene or tri- or tetrachlorobenzenes.

Aqueous preparations suitable for application can be prepared by the addition of water to emulsion concentrates, pastes or wettable powders. As emulsifying or dispersing agents there may be used non-ionic products, for example, condensation products of ethylene oxide with aliphatic alcohols, amines or carboxylic acids containing a hydrocarbon radical having about 10 to 30 carbon stoms, such as a condensation product of octadecyl alcohol with 25 to 30 molecular proportions of ethylene oxide, or of soy bean fatty acid with 30 molecular proportions of ethylene oxide or of commercial oleylamine with 15 molecular proportions of ethylene oxide or of dodecylmercaptan with 21 molecular proportions of ethylene-oxide. Among anion active emulsifying agents there may be mentioned the sodium salt of dodecyl alcohol sulfuric acid ester, the sodium salt of dodecyl-benzene sulfonic acid, the potassium or triethanolamine salt of oleic acid or abietic acid or of a mixture of these acids, or the sodium salt of petroleum-sulfonic acid. As cation-active dispersing agents there may be used quaternary ammonium compounds, such as cetyl-pyridinium bromide or di(hydroxyethyl)-benzyl-dodecyl ammonium chloride.

For making dusting or scattering preparations there may be used as solid carriers talcum, kaolin, bentonite, calcium carbonate or calcium phosphate or carbon, cork meal or wood meal or other materials of vegetable origin. The various preparations can be rendered more suitable for the various ways in which they are to be used by the known addition of substances which improve the dispersion, adhesiveness, resistance to rain or penetration capacity of the compositions. As such substances there may be mentioned fatty acids, resins, glues, casein or for example, alginates or the like. It is of considerable advantage to make up the preparation in granular form.

The herbicidal preparations of this invention are suitable, depending on the concentration in which they are used, for the selective destruction of weeds under crop plants and also for the total killing and destruction of undesired plant growth. The term "weeds" in used in this connection to include undesired plants, that is to say, plants previously planted or growing in the vicinity.

In the following examples there are described several preferred embodiments to illustrate the invention. However, it is to be understood that the invention is not intended to be limited to the specific embodiments.

EXAMPLE 1

240.2 g of dinoseb were added with stirring at room temperature to a 45% solution of 121.18 g of choline in methanol and the mixture was stirred for five minutes. Filtration of the mixture resulted in the recovery of 343.38 g of the choline salt of dinoseb melting at 37° C.

EXAMPLE 2

A formulation for spraying was prepared by admixing 1,432.42 g of 95% dinoseb, 1,542.23 g of 45% solution of choline in methanol, 635.02 g of methanol, 272.16 g of Hampene 100 (a 40% solution of tetrasodium ethylenediaminetetraacetate in water), 45.35 g of Polyfon H 28% (a 28% of Kraft processed sulfonated lignin) and 241.17 g of water to make one gallon of spray solution.

The said formulation was applied with a directed and a topical spray to cotton crops 3" and 28" tall infested with morning glory, cocklebut, ballonvine and grasses of the panicum genus as weeds. The spray gallonage was 50 gallons per acre wich was equivalent to 4 quarts of active herbicide per acre. At the time of application, the temperature was 85° F. and the weather was sunny with winds of 5 to 10 mph. The temperatures after application ranged from 70° to 90° F. with light winds and 50% to 80% humidity with no precipitation the next 4 days. Herbicidal readings were made 24 and 72 hours later and the results are reported in Table I.

TABLE I

| Species | Spray | Readings after hours | |
| --- | --- | --- | --- |
| | | 24 | 72 |
| 3" tall cotton | directed | no damage | no damage |
| | topical | 30% necrosis | 50% necrosis-regrowth |
| 28" tall cotton | directed | no damage | no damage |
| | topical | 30% necrosis | 40% necrosis-abundant regrowth |
| 3" tall cocklebur | topical | 90% necrosis | 100% necrosis |
| 18" tall cocklebur | topical | 80% necrosis | 100% necrosis |
| 4" tall morning glory | topical | 90% necrosis | 100% necrosis |
| 14" tall morning glory | topical | 84% necrosis | 99% necrosis |
| 15" tall ballon-vine | topical | 80% necrosis | 100% necrosis |
| 5" tall panicum | topical | 40% necrosis | 50% necrosis |

The results of Table I show that the weed control of the choline salt of dinoseb was excellent, particularly against broad leaf weeds and while there was some minor darkening of the areas of the cotton plants in contact therewith, there was no permanent damage. Residue after 72 hours was noticeably less indicating breakdown of the salt similar to other dinoseb derivatives.

EXAMPLE 3

A second field test was conducted with a spray formulation similar to that of Example 2 on cotton plots measuring 15'×15' with weeds of crabgrass, prickley sida, bluegrass, ragweed and common pigweed. Three tests were run with a spray gallonage of 50 gallons per acre. At the time of application, the temperature was 76° F. and the weather was sunny with calm winds. Moderate temperatures prevailed the next four days and on the fifth day there was a slight frost but evaluations were made on that day prior to any visible frost damages. Similar tests were simultaneously conducted with alkanolamine salts of dinoseb and the results are reported in Table II.

TABLE II

| Active ingredient | Dosage in quarts/acre | % overall weed control |
| --- | --- | --- |
| choline salt of dinoseb | 2 | 31% |
| | 3 | 54% |
| | 4 | 63% |
| + X-77 | 2 + 2 | 34% |
| alkanolamine salt of dinoseb | 2 | 34% |
| | 4 | 69% |
| + x 77 | 2 + 2 | 37% |

X-77 is a nonionic water-miscible liquid spray adjuvant acting as a wetting agent, spreader, penetrant and aid to penetration and is a common surfactant used to enhance pesticide performance.

The results of Table II show that the choline salt of dinoseb has the same efficacy as the alkanolamine salt of dinoseb. However, the salt of the invention does not form nitrosamines during or after formulation.

EXAMPLE 4

A field test in Kansas was conducted on soybeans 14 to 16 inches tall with 10 to 14 inch velvetleaf, 8 to 12 inch common ragweed and 6 to 12 inch smooth pigweed in three repetitive tests on 4 rows by 45 feet. The application was made under partly overcast skies with a 0 to 3 mph wind at 88° F. and 54% relative humidity. Readings were taken after 8 days and are reported in Table III. The three named weeds were used for test reporting but other weed species were also comparably controlled.

TABLE III

| Rate/Acre | % Soybean Injury | % Weed Control |
| --- | --- | --- |
| Choline Salt | | |
| 1 quart | 5 | 31 |
| 2 quarts | 5 | 46 |
| 3 quarts | 10 | 59 |
| Alkanolamine Salt | | |
| 1 quart | 5 | 28 |
| 2 quarts | 10 | 47 |
| 3 quarts | 10 | 56 |

EXAMPLE 5

A field test was conducted in Kansas on Golden Harvest 2500 field corn 5 to 5½ feet tall with no weeds present and three tests were run with two rows by 20 feet. The skies were overcast with a wind of 2 to 5 mph at 86° F. and 88% relative humidity. The results were taken after 8 days and are reported in Table IV.

TABLE IV

| Rate/Acre | % Corn Injury |
|---|---|
| Choline Salt | |
| 1 quart | 7 |
| 2 quarts | 20 |
| Alkanolamine Salt | |
| 1 quart | 8 |
| 2 quarts | 20 |

No stunting or chlorosis of the corn was observed from any treatment. Evaluation for selectivity of choline dinoseb salt herbicide gave similar results on peanuts, peas, beans, fruit and nut orchards, etc.

EXAMPLE 6

Tests in Tennessee were conducted on soybeans 20 to 22 inches tall with infestation with small and large cocklebur, small morning glory and prickly sida among other weeds. Three tests with 40 rows by 50 feet and the skies were overcast with no wind at 83° F. and 92% relative humidity. Readings were taken after 8 days and the results are reported in Table V.

TABLE V

| Rate/Acre | % Soybean leaf burn | % Soybean leaf curl | % Weed Control |
|---|---|---|---|
| Choline Salt | | | |
| 2 quarts | 30 | 10 | 68 |
| 3 quarts | 35 | 20 | 86 |
| Alkanolamine Salt | | | |
| 2 quarts | 25 | 15 | 71 |
| 3 quarts | 35 | 25 | 90 |

Various modifications of the compositions of the invention may be made without departing from the spirit or scope thereof and it should be understood that the invention is intended to be limited only as defined in the appended claims.

What I claim is:

1. The salt of 6-sec.-butyl-2,4-dinitrophenol and choline of the formula

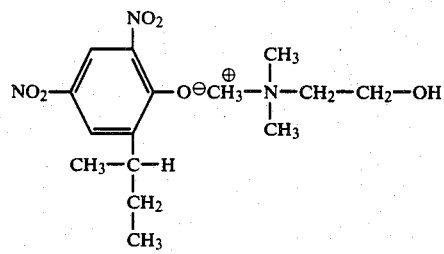

2. A selective herbicidal composition comprising an herbicidally effective amount of the choline salt of dinoseb and an inert carrier.

3. The composition of claim 2 wherein the composition is a liquid formulation.

4. A method of selectively controlling weeds in useful crops comprising applying to fields of a useful crop an herbicidally effective amount of the choline salt of dinoseb.

5. The method of claim 4 wherein the useful crop is selected from the group consisting of cotton, beans, corn, peanuts, soybeans potatoes, lentils, curcurbits, fruit and nut orchards, grapevines, peas and strawberries.

* * * * *